(12) United States Patent
Hashimoto

(10) Patent No.: US 7,961,928 B2
(45) Date of Patent: Jun. 14, 2011

(54) VOLUMETRIC DATA CONNECTING APPARATUS AND METHOD

(75) Inventor: Hiroshi Hashimoto, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 763 days.

(21) Appl. No.: 12/034,733

(22) Filed: Feb. 21, 2008

(65) Prior Publication Data
US 2009/0214120 A1 Aug. 27, 2009

(30) Foreign Application Priority Data
Feb. 23, 2007 (JP) ................. 2007-043079

(51) Int. Cl.
G06K 9/00 (2006.01)
(52) U.S. Cl. ........................................ 382/131
(58) Field of Classification Search .................. 382/131, 382/132
See application file for complete search history.

(56) References Cited

U.S. PATENT DOCUMENTS

| 6,157,797 A | 12/2000 | Saito et al. |
| 6,222,566 B1 | 4/2001 | Takeyama et al. |
| 6,574,361 B1* | 6/2003 | Kawakami et al. ........... 382/154 |
| 6,919,911 B2 | 7/2005 | Takeyama et al. |
| 2003/0065260 A1* | 4/2003 | Cheng et al. .................. 600/427 |
| 2005/0004449 A1* | 1/2005 | Mitschke et al. ............. 600/424 |
| 2007/0280522 A1 | 12/2007 | Sugiyama |

FOREIGN PATENT DOCUMENTS
JP 2007-021193 2/2007
* cited by examiner

Primary Examiner — Matthew C Bella
Assistant Examiner — Dennis Rosario
(74) Attorney, Agent, or Firm — Armstrong Teasdale LLP

(57) ABSTRACT

A volumetric data connecting apparatus, includes a reference point determining device for having an operator determine reference points A, B and C which are not on the same straight line on first volumetric data V; a connection point a determining device for having the operator determine a connection point a corresponding to said reference point A on second volumetric data v; an auxiliary line q displaying device for displaying "a section fb of the second volumetric data v" selected by the operator and a curve q which results from the crossing of said section fb and "a spherical surface Q having the distance between the reference points AB as its radius and the connection point a as its center".

20 Claims, 9 Drawing Sheets (a)

(b)

Individual coordinate volumetric data

US 7,961,928 B2

VOLUMETRIC DATA CONNECTING APPARATUS AND METHOD

CROSS REFERENCE TO RELATED APPLICATIONS

This application claims the benefit of Japanese Patent Application No. 2007-043079 filed Feb. 23, 2007.

BACKGROUND OF THE INVENTION

The field of the present invention relates to a volumetric data connecting apparatus and method, and more particularly to a volumetric data connecting apparatus that facilitates connection of two volumetric data.

Conventional apparatuses that automatically connect volumetric data are known (see Patent Document 1 for instance).

Patent Document 1. Japanese Unexamined Patent Publication No. 2007-021193.

As a matter of practice, it is difficult to automatically connect two volumetric data obtained by an image diagnostic apparatus such as an ultrasonic diagnostic apparatus or an X-ray CT apparatus, and the current practice is to connect two volumetric data by having the operator visually recognize and designate three or more corresponding characteristic points in the two volumetric data.

However, visually recognizing and designating corresponding characteristic points in two volumetric data involves the problem of imposing a heavy load on the operator.

SUMMARY OF THE INVENTION

It is desirable that the problem described previously is solved.

In a first aspect, the invention provides a volumetric data connecting apparatus comprising: reference point determining device for having an operator determine reference points A, B and C which are not on the same straight line on first volumetric data V; connection point a determining device for having the operator determine a connection point a corresponding to the reference point A on second volumetric data v; auxiliary line q displaying device for displaying "a section fb of the second volumetric data v" selected by the operator and a curve q which results from the crossing of the section fb and "a spherical surface Q having the distance between the reference points AB as its radius and the connection point a as its center"; connection point b determining device for having the operator determine a connection point b corresponding to the reference point B on the section fb; auxiliary lines rt displaying device for displaying "a section fc of the second volumetric data v" selected by the operator, a curve r which results from the crossing of the section fc and "a spherical surface R having the distance between the reference points AC as its radius and the connection point a as its center" and a curve t which results from the crossing of the section fc and "a spherical surface T having the distance between the reference points BC as its radius and the connection point b as its center"; connection point c determining device for having the operator determine a connection point c corresponding to the reference point C on the section fc; and coordinate adjusting device for so adjusting the coordinates of the first volumetric data V and the second volumetric data v that the reference points A, B and C and the connection points a, b and c have respectively the same coordinates.

With the volumetric data connecting apparatus according to the first aspect, when to determine the connection point b, the operator can search for it with the displayed auxiliary line q as a yardstick. Also, when to determine the connection point c, the operator can search for it with the intersection of the displayed auxiliary lines r and t as a yardstick. Therefore, the load on the operator can be reduced.

Incidentally, it is assumed here that the first volumetric data V and the second volumetric data v are two volumetric data picked up under the same conditions except that the position and angle of the ultrasonic probe slightly differ.

According to a second aspect, the invention provides a volumetric data connecting apparatus according to the first aspect, comprising, in place of the auxiliary lines rt displaying device or in addition to the auxiliary lines rt displaying device, intersection displaying device for displaying "the section fc of the second volumetric data v" selected by the operator and the intersection between the curve r which results from the crossing of the section fc and "the spherical surface R having the distance between the reference points AC as its radius and the connection point a as its center" and the curve t which results from the crossing of the section fc and "the spherical surface T having the distance between the reference points BC as its radius and the connection point b as its center".

With the volumetric data connecting apparatus according to the second aspect, when to determine the connection point c, the operator can search for it with the displayed intersection of the displayed auxiliary lines r and t as a yardstick. Therefore, the load on the operator can be reduced.

According to a third aspect, the invention provides a volumetric data connecting apparatus according to the first or second aspect, wherein the second volumetric data v comprises a plurality of frames and each of the sections fb and fc is one of the frames.

The volumetric data connecting apparatus according to the third aspect, since the sections fb and fc are among the plurality of frames of the second volumetric data v, makes the processing to calculate the sections unnecessary.

According to a fourth aspect, the invention provides a volumetric data connecting apparatus comprising: reference point determining device for having an operator determine reference points A, B and C which are not on the same straight line on first volumetric data V; connection points ab determining device for having the operator determine a connection point a corresponding to the reference point A and a connection point b corresponding to the reference point B on second volumetric data v; auxiliary lines rt displaying device for displaying "a section fc of the second volumetric data v" selected by the operator, a curve r which results from the crossing of the section fc and "a spherical surface R having (the distance between the reference points AC)×(the distance between the connection points ab)÷(the distance between the reference points AB) as its radius and the connection point a as its center" and a curve t which results from the crossing of the section fc and "a spherical surface T having (the distance between the reference points BC)×(the distance between the connection points ab)÷(the distance between the reference points AB) as its radius and the connection point b as its center"; connection point c determining device for having the operator determine a connection point c corresponding to the reference point C on the section fc; and coordinate adjusting device for so adjusting the coordinates of the first volumetric data V and the second volumetric data v that the reference points A, B and C and the connection points a, b and c have respectively the same coordinates.

With the volumetric data connecting apparatus according to the fourth aspect, when to determine the connection point c, the operator can search for it with the displayed intersection of the displayed auxiliary lines r and t as a yardstick. Therefore, the load on the operator can be reduced.

Incidentally the first volumetric data V and the second volumetric data v may have different reduced scales. For instance, they may be volumetric data picked up with an ultrasonic diagnostic apparatus and volumetric data picked up with an X-ray CT apparatus.

According to a fifth aspect, the invention provides a volumetric data connecting apparatus according to the fourth aspect, comprising, in place of the auxiliary lines rt displaying device or in addition to the auxiliary lines rt displaying device, intersection displaying device for displaying "the section fc of the second volumetric data v" selected by the operator and the intersection between the curve r which results from the crossing of the section fc and "the spherical surface R having (the distance between the reference points AC)×(the distance between the connection points ab)÷(the distance between the reference points AB) as its radius and the connection point a as its center" and the curve t which results from the crossing of the section fc and "the spherical surface T having (the distance between the reference points BC)×(the distance between the connection points ab)÷(the distance between the reference points AB) as its radius and the connection point b as its center".

With the volumetric data connecting apparatus according to the fifth aspect, when to determine the connection point c, the operator can search for it with the displayed intersection as a yardstick. Therefore, the load on the operator can be reduced.

According to a sixth aspect, the invention provides a volumetric data connecting apparatus according to the fourth or fifth aspect, wherein the second volumetric data v comprises a plurality of frames and the section fc is one of the frames.

The volumetric data connecting apparatus according to the sixth aspect, since the section fc is one of the plurality of frames of the second volumetric data v, makes the processing to calculate the section unnecessary.

According to a seventh aspect, the invention provides a volumetric data connecting apparatus according to any of the first through sixth aspects, comprising volumetric data capturing device for capturing from outside the first volumetric data V and the second volumetric data v.

The volumetric data connecting apparatus according to the seventh aspect can connect volumetric data obtained by external apparatuses.

According to an eighth aspect, the invention provides a volumetric data connecting apparatus according to any of the first through seventh aspects, comprising volumetric data capturing device for capturing from an image diagnostic apparatus the first volumetric data V and the second volumetric data v.

The volumetric data connecting apparatus according to the eighth aspect can connect volumetric data obtained by an image diagnostic apparatus.

According to a ninth aspect, the invention provides a volumetric data connecting method comprising: a reference point determining step for having an operator determine reference points A, B and C which are not on the same straight line on first volumetric data V; a connection point a determining step for having the operator determine a connection point a corresponding to the reference point A on second volumetric data v; an auxiliary line q displaying step for displaying "a section fb of the second volumetric data v" selected by the operator and a curve q which results from the crossing of the section fb and "a spherical surface Q having the distance between the reference points AB as its radius and the connection point a as its center"; a connection point b determining step for having the operator determine a connection point b corresponding to the reference point B on the section fb; an auxiliary lines rt displaying step for displaying "a section fc of the second volumetric data v" selected by the operator, a curve r which results from the crossing of the section fc and "a spherical surface R having the distance between the reference points AC as its radius and the connection point a as its center" and a curve t which results from the crossing of the section fc and "a spherical surface T having the distance between the reference points BC as its radius and the connection point b as its center"; a connection point c determining step for having the operator determine a connection point c corresponding to the reference point C on the section fc; and a coordinate adjusting step for so adjusting the coordinates of the first volumetric data V and the second volumetric data v that the reference points A, B and C and the connection points a, b and c have respectively the same coordinates.

By the volumetric data connecting method according to the ninth aspect, when to determine the connection point b, the operator can search for it with the displayed auxiliary line q as a yardstick. Also, when to determine the connection point c, the operator can search for it with the intersection of the displayed auxiliary lines r and t as a yardstick. Therefore, the load on the operator can be reduced.

Incidentally, it is assumed here that the first volumetric data V and the second volumetric data v are two volumetric data picked up under the same conditions except that the position and angle of the ultrasonic probe slightly differ.

According to a tenth aspect, the invention provides a volumetric data connecting method according to the ninth aspect, comprising, in place of the auxiliary lines rt displaying step or in addition to the auxiliary lines rt displaying step, an intersection displaying step for displaying "the section fc of the second volumetric data v" selected by the operator and the intersection between the curve r which results from the crossing of the section fc and "the spherical surface R having the distance between the reference points AC as its radius and the connection point a as its center" and the curve t which results from the crossing of the section fc and "the spherical surface T having the distance between the reference points BC as its radius and the connection point b as its center".

By the volumetric data connecting method according to the tenth aspect, when to determine the connection point c, the operator can search for it with the displayed intersection as a yardstick. Therefore, the load on the operator can be reduced.

According to an eleventh aspect, the invention provides a volumetric data connecting method according to the ninth or tenth aspect, wherein the second volumetric data v comprises a plurality of frames and each of the sections fb and fc is one of the frames.

The volumetric data connecting method according to the eleventh aspect, since the sections fb and fc are among the plurality of frames of the second volumetric data v, makes the processing to calculate the sections unnecessary.

According to a twelfth aspect, the invention provides a volumetric data connecting method comprising: a reference point determining step for having an operator determine reference points A, B and C which are not on the same straight line on first volumetric data V; a connection points ab determining step for having the operator determine a connection point a corresponding to the reference point A and a connection point b corresponding to the reference point B on second volumetric data v; an auxiliary lines rt displaying step for displaying "a section fc of the second volumetric data v" selected by the operator, a curve r which results from the crossing of the section fc and "a spherical surface R having (the distance between the reference points AC)×(the distance between the connection points ab)÷(the distance between the reference points AB) as its radius and the connection point a as its center" and a curve t which results from the crossing of the section fc and "a spherical surface T having (the distance between the reference points BC)×(the distance between the connection points ab)÷(the distance between the reference points AB) as its radius and the connection point b as its center"; a connection point c determining step for having the operator determine a connection point c corresponding to the reference point C on the section fc; and a coordinate adjusting step for so adjusting the coordinates of the first volumetric data V and the second volumetric data v that the reference points A, B and C and the connection points a, b and c have respectively the same coordinates.

By the volumetric data connecting method according to the twelfth aspect, when to determine the connection point c, the operator can search for it with the displayed intersection of the displayed auxiliary lines r and t as a yardstick. Therefore, the load on the operator can be reduced.

Incidentally the first volumetric data V and the second volumetric data v may have different reduced scales. For instance, they may be volumetric data picked up with an ultrasonic diagnostic apparatus and volumetric data picked up with an X-ray CT apparatus.

According to a thirteenth aspect, the invention provides a volumetric data connecting method according to the twelfth aspect, comprising, in place of the auxiliary lines rt displaying step or in addition to the auxiliary lines rt displaying step, an intersection displaying step for displaying "the section fc of the second volumetric data v" selected by the operator and the intersection between the curve r which results from the crossing of the section fc and "the spherical surface R having (the distance between the reference points AC)×(the distance between the connection points ab)÷(the distance between the reference points AB) as its radius and the connection point a as its center" and the curve t which results from the crossing of the section fc and "the spherical surface T having (the distance between the reference points BC)×(the distance between the connection points ab)÷(the distance between the reference points AB) as its radius and the connection point b as its center".

By the volumetric data connecting method according to the thirteenth aspect, when to determine the connection point c, the operator can search for it with the displayed intersection as a yardstick. Therefore, the load on the operator can be reduced.

According to a fourteenth aspect, the invention provides a volumetric data connecting method according to the twelfth or thirteenth aspect, wherein second volumetric data v comprises a plurality of frames and the section fc is one of the frames.

The volumetric data connecting method according to the fourteenth aspect, since the section fc is one of the plurality of frames of the second volumetric data v, makes the processing to calculate the sections unnecessary.

According to a fifteenth aspect, the invention provides a volumetric data connecting method according to any of the ninth through fourteenth aspect, comprising a volumetric data capturing step for capturing from outside the first volumetric data V and the second volumetric data v.

The volumetric data connecting method according to the fifteenth aspect can connect volumetric data obtained by external apparatuses.

According to a sixteenth aspect, the invention provides a volumetric data connecting method according to any of the ninth through fifteenth aspect, comprising a volumetric data capturing step for capturing by an image diagnostic method the first volumetric data V and the second volumetric data v.

The volumetric data connecting method according to the sixteenth aspect can connect volumetric data obtained by an image diagnostic apparatus.

As the volumetric data connecting apparatus and method according to the invention indicate yardsticks of the area which the operator should search for characteristic points for connecting two volumetric data, the load of visually recognizing and designating corresponding characteristic points on the operator can be reduced.

The volumetric data connecting apparatus and method according to the invention can be utilized for spatially connecting, for instance, volumetric data obtained by three-dimensional ultrasonic imaging with an ultrasonic diagnostic apparatus and volumetric data obtained by helical scanning with an X-ray CT apparatus.

Further objects and advantages of the present invention will be apparent from the following description of the preferred embodiments of the invention as illustrated in the accompanying drawings.

BRIEF DESCRIPTION OF THE DRAWINGS

FIG. 7 is a schematic diagram showing an example of screen for determining the connection point a.

DETAILED DESCRIPTION OF THE INVENTION

The best modes for carrying out the invention will be described in detail with reference to drawings. Incidentally, this description is nothing to limit the invention.

Figure 1:
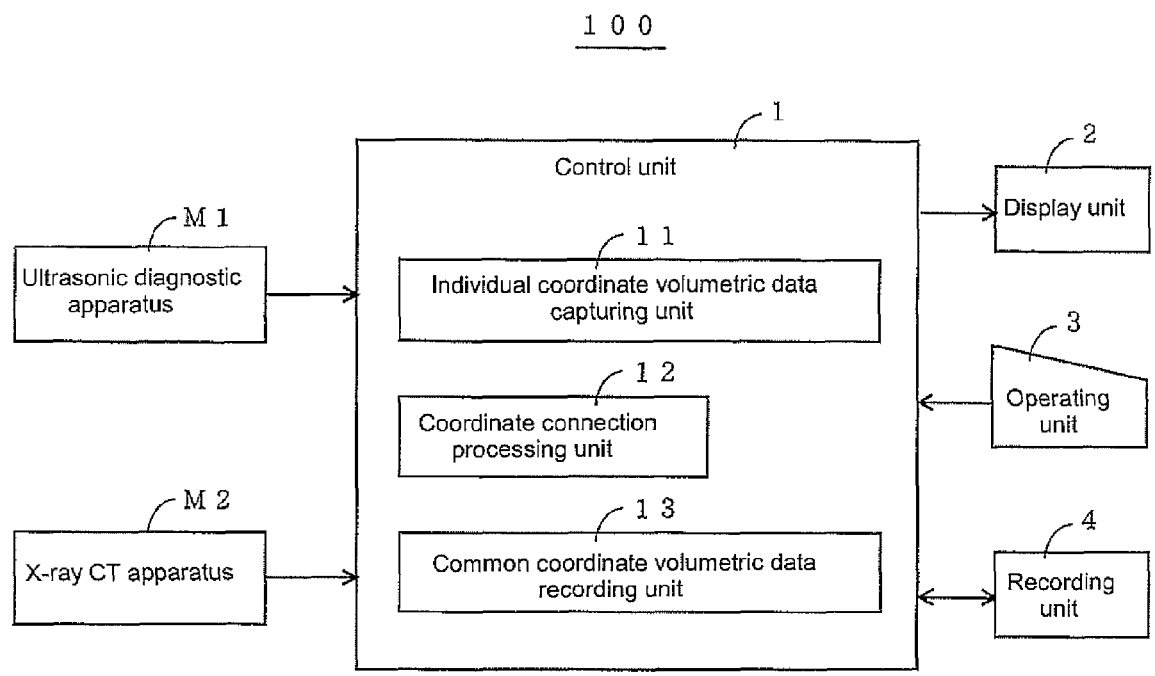
FIG. 1 is a block diagram showing the configuration of a volumetric data connecting apparatus 100 pertaining to Embodiment 1.

Embodiment 1. FIG. 1 is a block diagram showing the configuration of a volumetric data connecting apparatus 100 pertaining to Embodiment 1.

This volumetric data connecting apparatus 100 is equipped with a control unit 1, a display unit 2, an operating unit 3, and a recording unit 4.

The control unit 1 comprises an individual coordinate volumetric data capturing unit 11 for capturing volumetric data from an external medical image diagnostic apparatus such as an ultrasonic diagnostic apparatus M1 or an X-ray CT apparatus M2, a coordinate connection processing unit 12 for connecting two volumetric data which have been captured, and a common coordinate volumetric data recording unit 13 for recording the connected two volumetric data.

Figure 2:
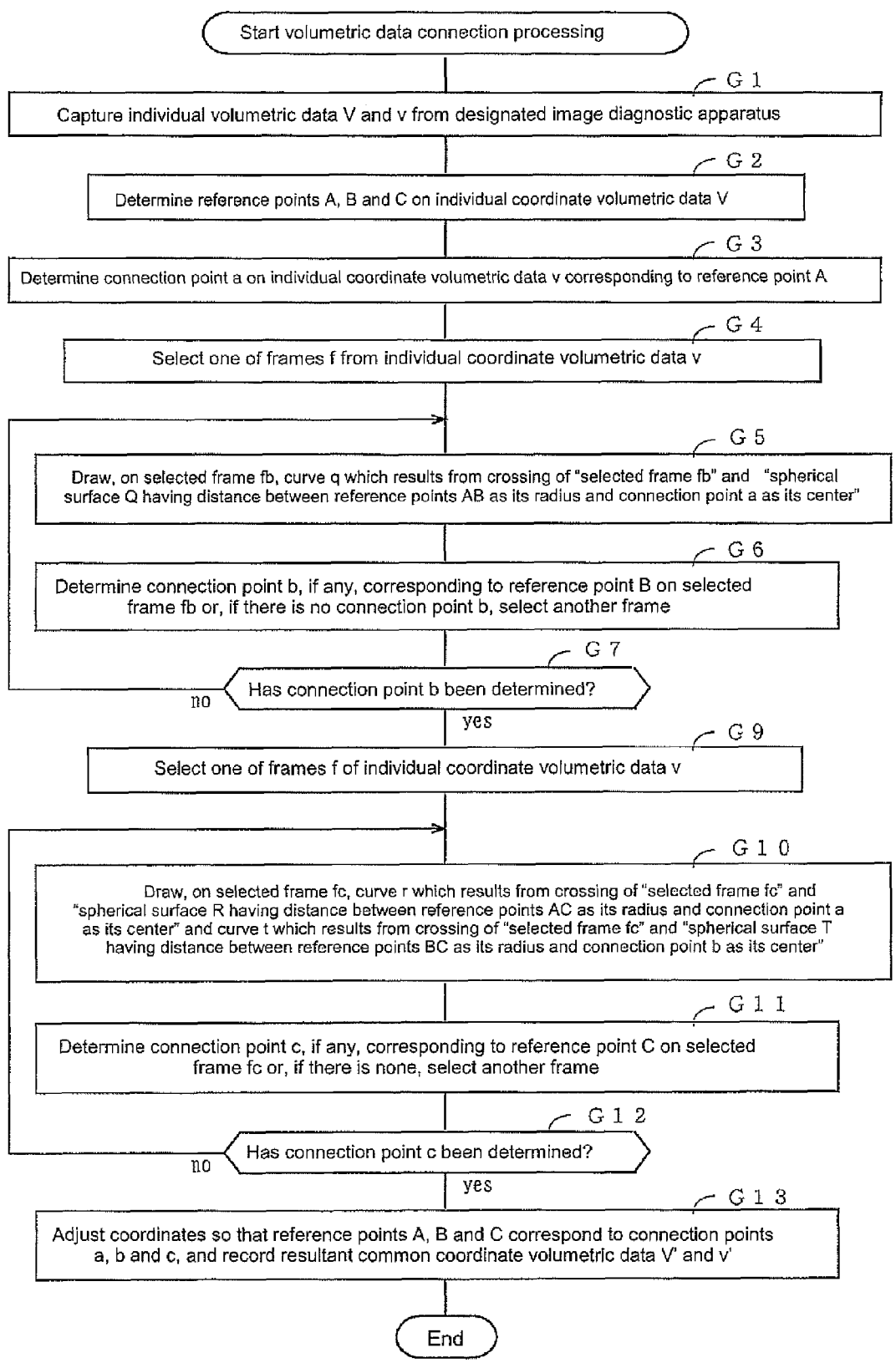
FIG. 2 is a flow chart showing the volumetric data connection processing pertaining to Embodiment 1.

FIG. 2 is a flow chart showing the volumetric data connection processing by the volumetric data connecting apparatus 100.

At step G1, the operator is caused to designate the image diagnostic apparatus that is to be the source of capturing volumetric data, and the volumetric data are captured from the designated image diagnostic apparatus.

Figure 3:
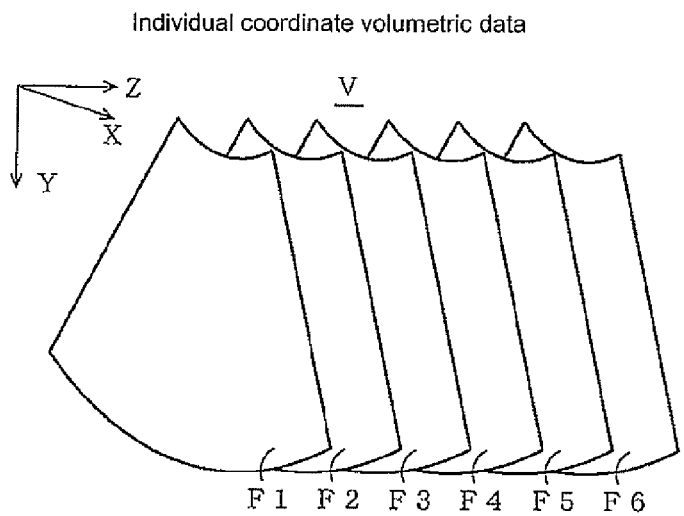
FIG. 3 is a conceptual diagram showing the first volumetric data.
Figure 4:
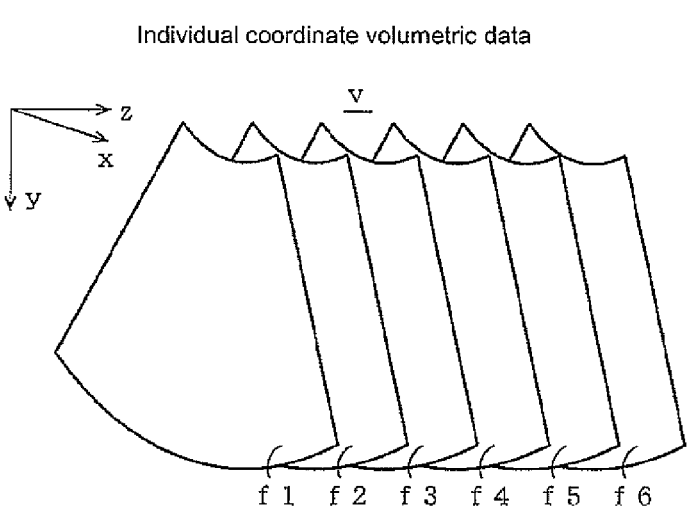
FIG. 4 is a conceptual diagram showing the second volumetric data.

It is supposed here that first volumetric data V shown in FIG. 3 and second volumetric data v shown in FIG. 4, picked up under the same conditions as the first volumetric data V except that the position and angle of the ultrasonic probe slightly differ, are captured from the ultrasonic diagnostic apparatus M1. Since the spatial coordinates XYZ of the first volumetric data V and the spatial coordinates xyz of the second volumetric data v are different spatial coordinates because of the differences in the position and angle of the ultrasonic probe, they will be referred to as individual coordinate volumetric data V and v, respectively. The individual coordinate volumetric data V is supposed to consist of a plurality of spatially arrayed frames F1 through F6, and the individual coordinate volumetric data v is also supposed to consist of a spatially arrayed plurality of frames f1 through f6.

Figure 5:
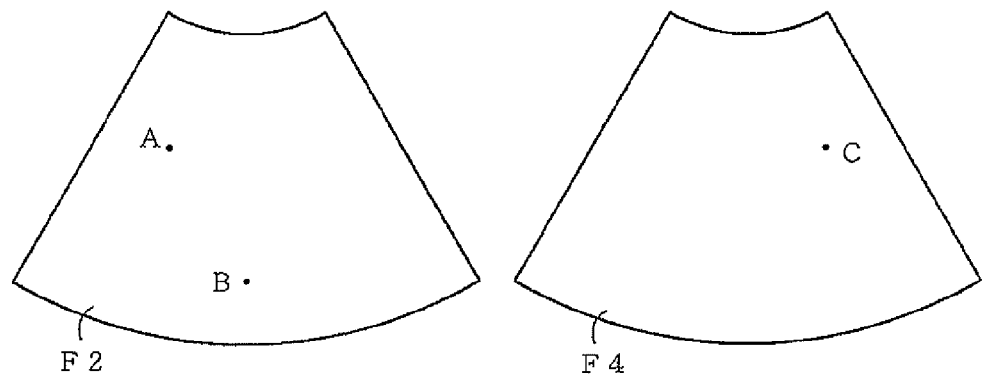
FIG. 5 is a schematic diagram showing an example of screen for determining the reference points A, B and C.
Figure 6:
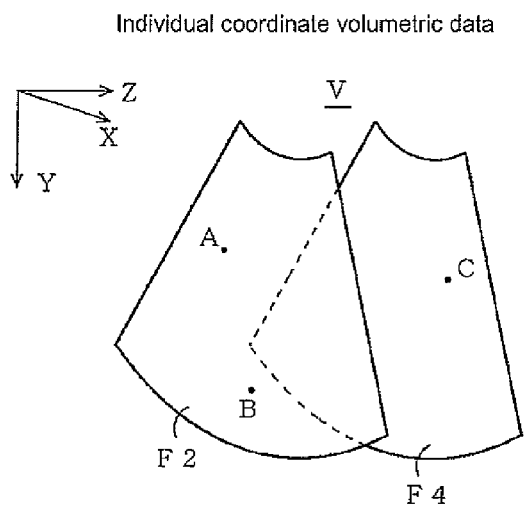
FIG. 6 is a perspective view showing the spatial arrangement of the reference points A, B and C.

At step G2, the operator is caused to determine reference points A, B and C that are not on the same straight line on the individual coordinate volumetric data V. For instance, the operator determines the reference points A and B on the frame F2 and the reference point C on the frame F4 of the individual coordinate volumetric data V as shown in FIG. 5. The spatial arrangement of the reference points A, B and C is shown in FIG. 6. Incidentally, the number of reference points may be four or more.

Figure 7:
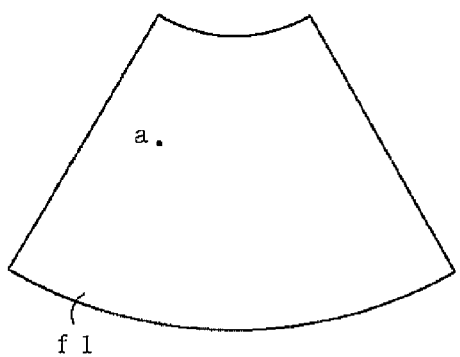

At step G3, the operator is caused to determine a connection point a on the individual coordinate volumetric data v corresponding to the reference point A. The operator determines the connection point a on the frame f1 of the individual coordinate volumetric data v as shown in FIG. 7.

At step G4, the operator is caused to select one of frames f1 through f6 of the individual coordinate volumetric data v. The selected frame will be referred to as the frame fb.

Figure 8:
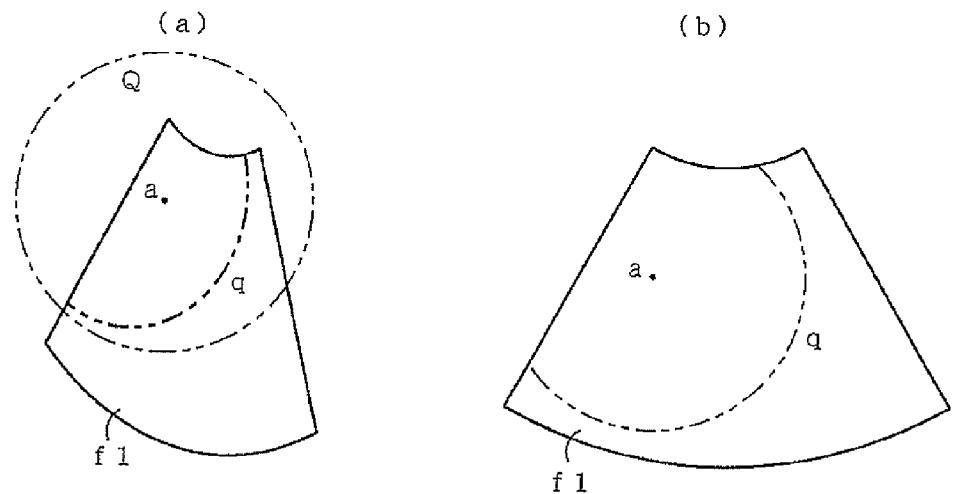
FIGS. 8(a) and 8(b) are schematic diagrams comprising a perspective view of the curve q and an example of screen depicting the curve q.

At step G5, the frame fb is displayed, and a curve q which results from the crossing of "the frame fb" and "a spherical surface Q having the distance between the reference points AB as its radius and the connection point a as its center" is drawn on the frame fb. For instance, if the operator has selected the frame f1, the curve q resulting from the crossing of the frame f1 and the spherical surface Q as shown in FIG. 8(a) is calculated, and the frame f1 and the curve q are displayed as shown in FIG. 8(b).

At step G6, the operator is caused to determine a connection point b, if any, corresponding to the reference point B on the displayed frame fb or, if there is no connection point b, to select another frame.

Figure 9:
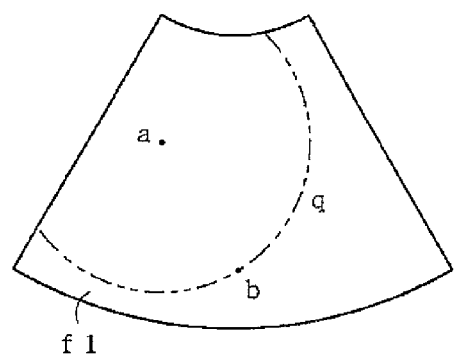
FIG. 9 is a schematic diagram showing an example of screen for determining the connection point b.

It is supposed here that, as a connection point b has been found on the curve q of the displayed frame f1 as shown in FIG. 9, the operator has determined the connection point b.

From step G7, if the connection point b has been determined, the processing advances to step G9 or, if another frame has been selected, it will return to step G5.

At step G9, the operator is caused to select one of frames f1 through f6 of the individual coordinate volumetric data v. The selected frame will be referred to as the frame fc.

Figure 10:
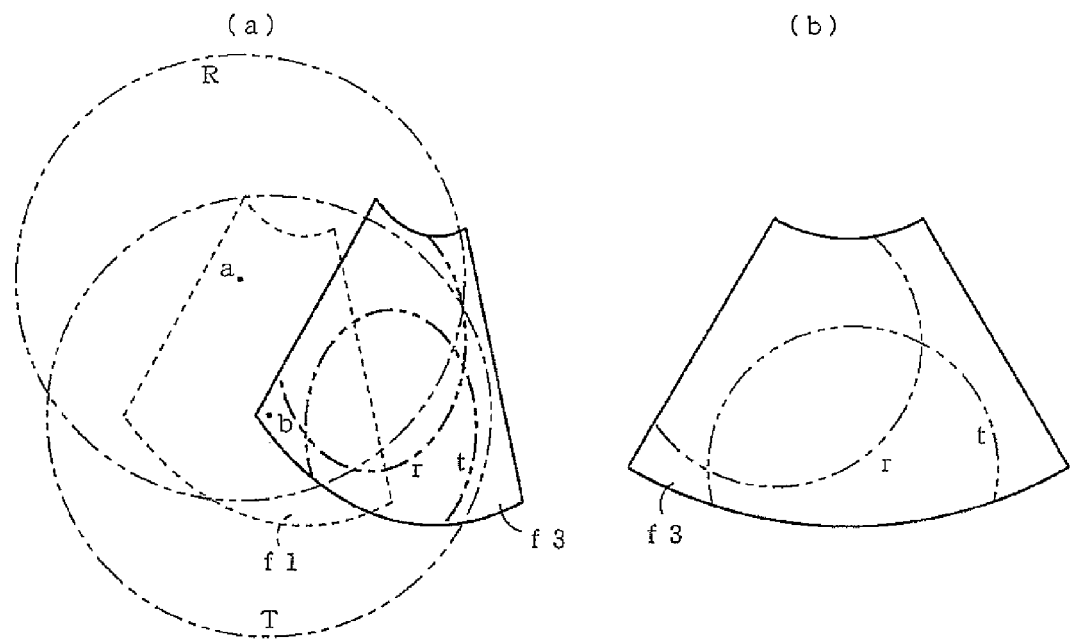
FIGS. 10(a) and 10(b) are schematic diagrams comprising a perspective view of the curves r and t and an example of screen depicting them.

At step G10, the frame fc is displayed, and a curve r which results from the crossing of "the frame fc" and "a spherical surface R having the distance between the reference points AC as its radius and the connection point a as its center" and a curve t which results from the crossing of "the frame fc" and "a spherical surface T having the distance between the reference points BC as its radius and the connection point b as its center" are drawn on the frame fc. For instance, if the operator has selected the frame f3, the curve r resulting from the crossing of the frame f3 and the spherical surface R as shown in FIG. 10(a) and a curve t resulting from the crossing of the frame f3 and a spherical surface T are calculated, and the frame f1 and the curves r and t are displayed as shown in FIG. 10(b).

At step G11, the operator is caused to determine a connection point c, if any, corresponding to the reference point C on the displayed frame fc or, if there is no connection point c, to select another frame.

Figure 11:
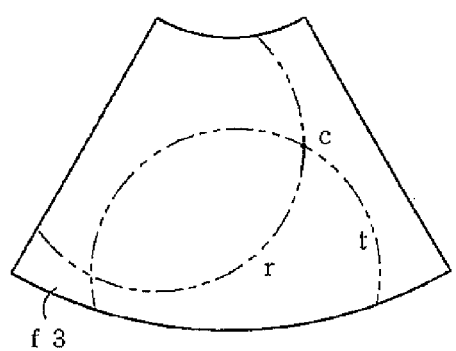
FIG. 11 is a schematic diagram showing an example of screen for determining the connection point c.

It is supposed here that, as a connection point c has been found at one of the intersections of between on the curves r and t of the displayed frame f3 as shown in FIG. 11, the operator has determined the connection point c.

From step G12, if the connection point c has been determined, the processing advances to step G13 or, if another frame has been selected, it will return to step G10.

Figure 12:
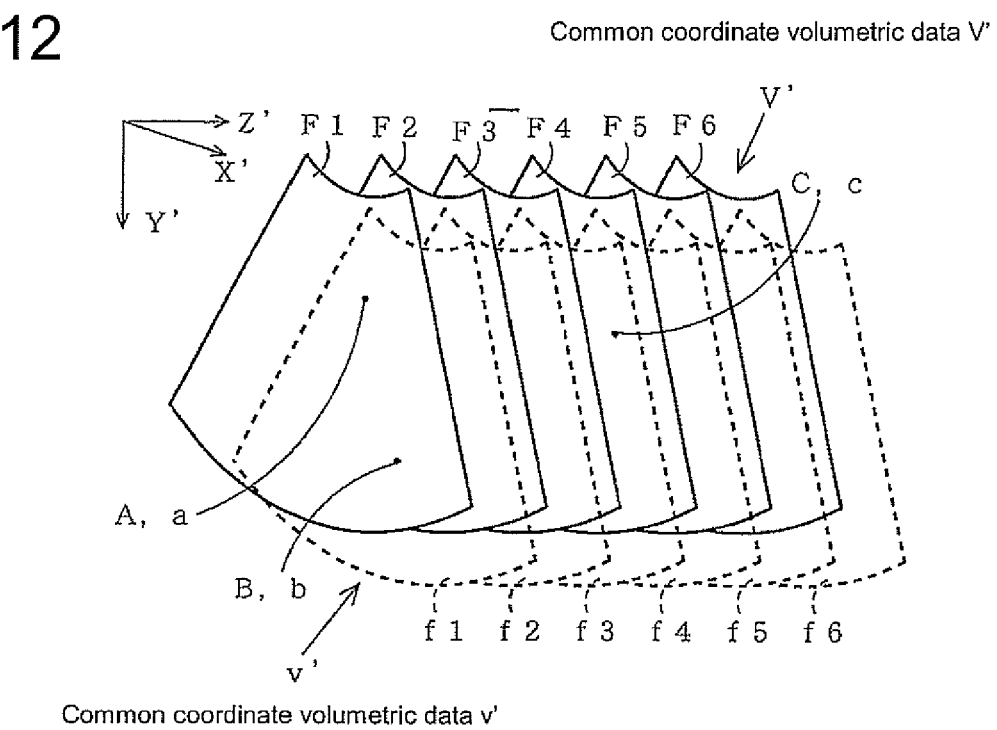
FIG. 12 is a conceptual diagram showing two connected volumetric data.

At step G13, as shown in FIG. 12, coordinates are so adjusted that the reference points A, B and C correspond to the connection points a, b and c, respectively. Thus, the volumetric data V is recorded as volumetric data V' on common coordinates X'Y'Z' and the volumetric data v, as volumetric data v' on common coordinates x'y'z', and the processing is ended.

With the volumetric data connecting apparatus 100 of Embodiment 1, when to determine the connection point b, the operator can search for it with a displayed auxiliary line q as a yardstick. Also, when to determine the connection point c, the operator can search for it with the intersection of displayed auxiliary lines r and t as a yardstick. Therefore, the load on the operator can be reduced.

Figure 13:
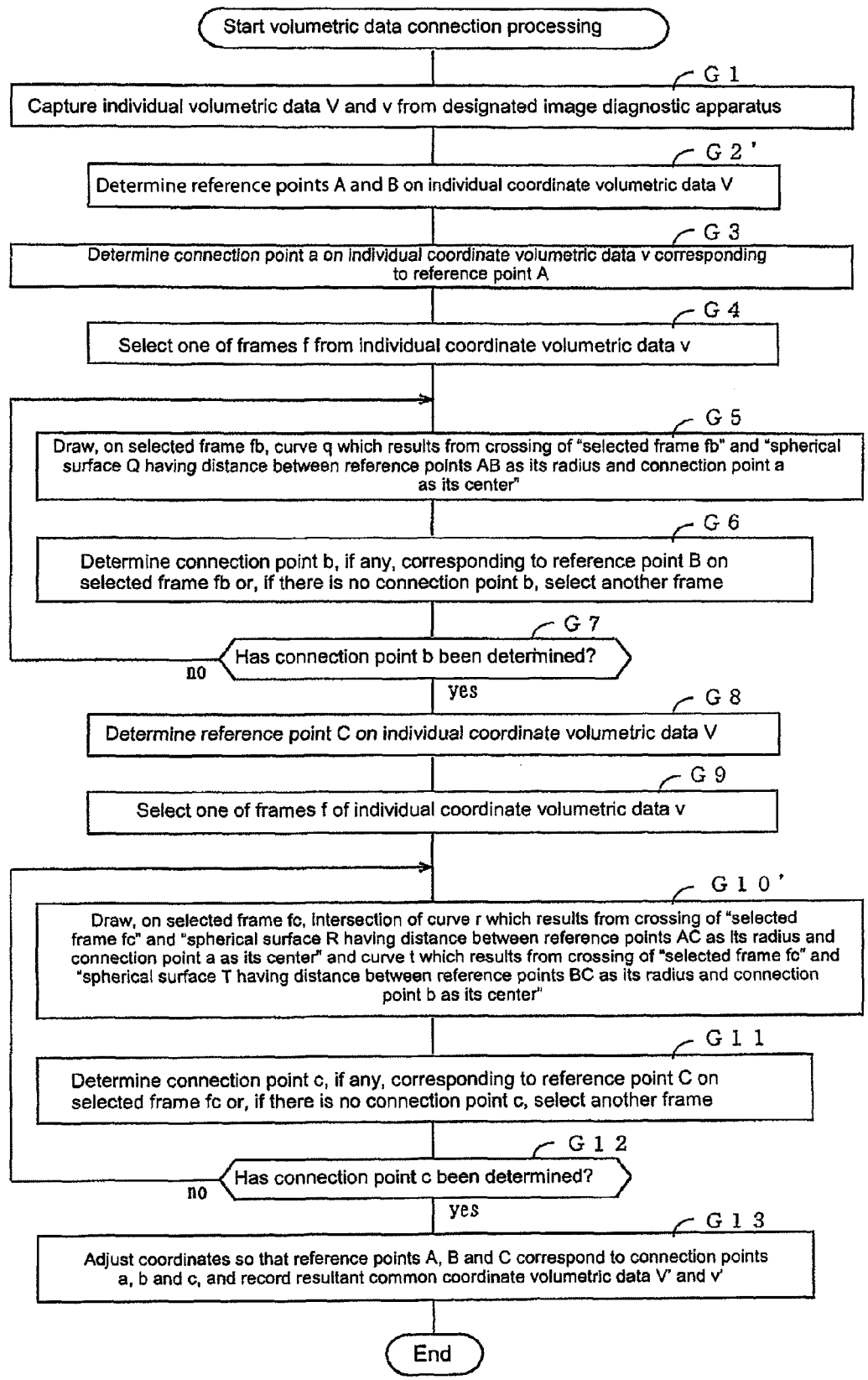
FIG. 13 is a flow chart showing the volumetric data connection processing pertaining to Embodiment 2.

Embodiment 2. FIG. 13 is a flow chart showing the volumetric data connection processing pertaining to Embodiment 2.

Since all other steps than steps G2', G8 and G10' are the same as their respective counterparts in FIG. 2, only steps G2', G8 and G10' will be described.

At step G2', the operator is caused to determine the reference points A and B on the individual coordinate volumetric data V.

At step G8, the operator is caused to determine the reference point C on the individual coordinate volumetric data V.

Figure 14:
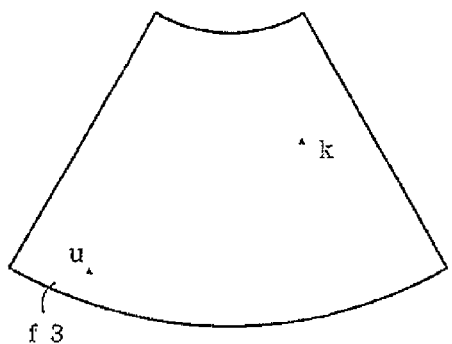
FIG. 14 is a schematic diagram showing an example of screen depicting intersections.

At step G10', the frame fc is displayed, and the intersection between the curve r which results from the crossing of the frame fc and the spherical surface R and the curve t which results from the crossing of the frame fc and the spherical surface T is drawn on the frame fc. For instance, the frame f3 and the intersections k and u between the curve r and the curve t are displayed as shown in FIG. 14.

By the volumetric data connection processing pertaining to Embodiment 2, when to determine the connection point b, the operator can search for it with the displayed auxiliary line q as a yardstick. Also, when to determine the connection point c, the operator can search for it with the displayed intersections k and u as yardsticks. Therefore, the load on the operator can be reduced.

Incidentally, both the curves r and t and the intersections k and u may be displayed.

Figure 15:
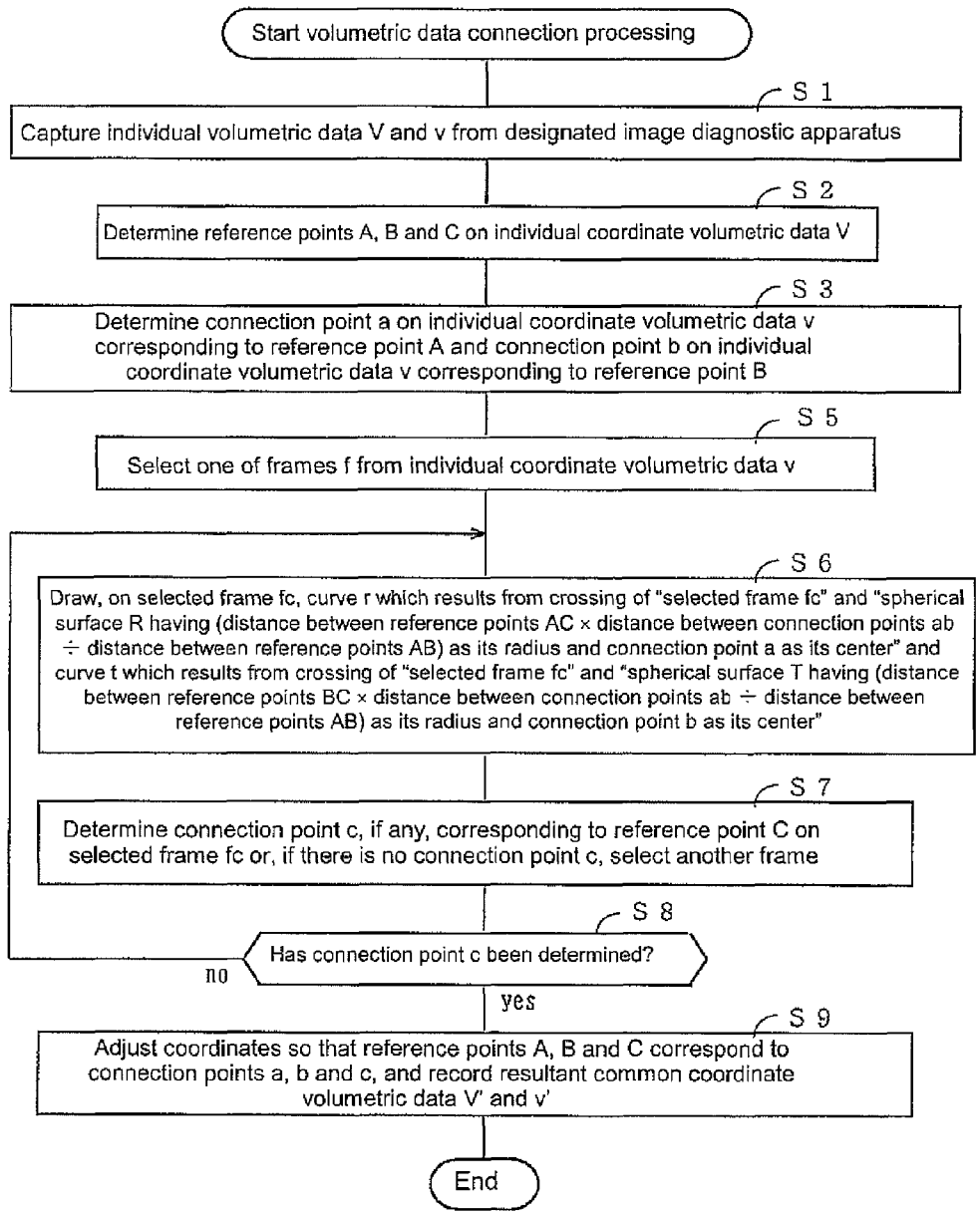
FIG. 15 is a flow chart showing the volumetric data connection processing pertaining to Embodiment 3.

Embodiment 3. FIG. 15 is a flow chart showing the volumetric data connection processing pertaining to Embodiment 3.

At step S1, the operator is caused to designate the image diagnostic apparatus that is to be the source of capturing volumetric data, and the volumetric data are captured from the designated image diagnostic apparatus.

It is supposed here that the first volumetric data V is captured from the ultrasonic diagnostic apparatus M1 and the second volumetric data v is captured from the X-ray CT apparatus M2. Since the spatial coordinates of the first volumetric data V and the spatial coordinates of the second volumetric data v are different spatial coordinates, they will be referred to as individual coordinate volumetric data V and v, respectively. The individual coordinate volumetric data V is supposed to consist of a plurality of spatially arrayed frames, and the individual coordinate volumetric data v is also supposed to consist of a spatially arrayed plurality of frames.

At step S2, the operator is caused to determine the reference points A, B and C that are not on the same straight line on the individual coordinate volumetric data V.

At step S3, the operator is caused to determine the connection point a on the individual coordinate volumetric data v corresponding to the reference point A and the connection point b on the individual coordinate volumetric data v corresponding to the reference point B.

At step S5, the operator is caused to select one of the frames of the individual coordinate volumetric data v. The selected frame will be referred to as the frame fc.

At step S6, the frame fc id displayed, and the curve r which results from the crossing of "the frame fc" and "the spherical surface R having (the distance between the reference points AC)×(the distance between the connection points ab)÷(the distance between the reference points AB) as its radius and the connection point a as its center" and the curve t which results from the crossing of "the frame fc" and "the spherical surface T having (the distance between the reference points BC)×(the distance between the connection points ab)÷(the distance between the reference points AB) as its radius and the connection point b as its center" are drawn on the frame fc.

At step S7, the operator is caused to determine the connection point c, if any, corresponding to the reference point C on the displayed frame fc or, if there is no connection point c, to select another frame.

From step S8, if the connection point c has been determined, the processing advances to step S9 or, if another frame has been selected, it will return to step S6.

At step S9, coordinates are so adjusted that the reference points A, B and C correspond to the connection points a, b and c, respectively. Thus, the volumetric data V is recorded as the volumetric data V' on the common coordinates X'Y'Z' and the volumetric data v, as the volumetric data v' on the common coordinates x'y'z', and the processing is ended.

By the volumetric data connection processing pertaining to Embodiment 3, when to determine the connection point c, the operator can search for it with the intersections of the displayed auxiliary lines r and t as yardsticks. Therefore, the load on the operator can be reduced.

Figure 16:
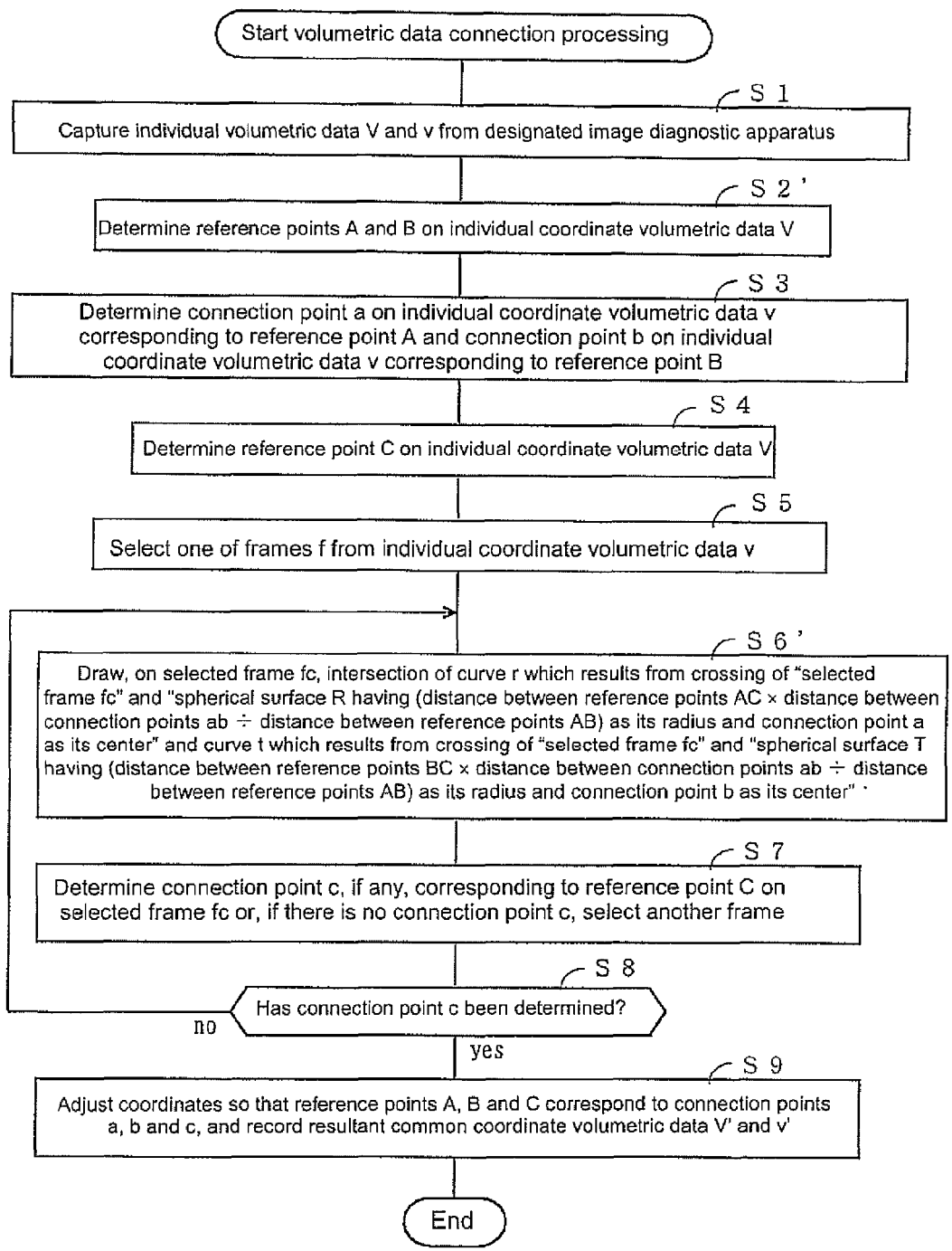
FIG. 16 is a flow chart showing the volumetric data connection processing pertaining to Embodiment 4.

Embodiment 4. FIG. 16 is a flow chart showing the volumetric data connection processing pertaining to Embodiment 4.

Since all other steps than steps S2', S4 and S6' are the same as their respective counterparts in FIG. 15, only steps S2', S4 and S6' will be described.

At step S2', the operator is caused to determine the reference points A and B on the individual coordinate volumetric data V.

At step S4, the operator is caused to determine the reference point C on the individual coordinate volumetric data V.

At step S6', the frame fc is displayed, and the intersection between the curve r which results from the crossing of the frame fc and the spherical surface R and the curve t which results from the crossing of the frame fc and the spherical surface T is drawn on the frame fc.

By the volumetric data connection processing pertaining to Embodiment 4, when to determine the connection point c, the operator can search for it with the displayed intersection as a yardstick. Therefore, the load on the operator can be reduced.

Incidentally, both the curves r and t and the intersections may be displayed.

Many widely different embodiments of the invention may be configured without departing from the spirit and the scope of the present invention. It should be understood that the present invention is not limited to the specific embodiments described in the specification, except as defined in the appended claims.

The invention claimed is:

1. A volumetric data connecting apparatus comprising:
a reference point determining device for having an operator determine reference points A, B and C which are not on the same straight line on first volumetric data V;
a connection points ab determining device for having the operator determine a connection point a corresponding to said reference point A and a connection point b corresponding to said reference point B on a second volumetric data v;
an auxiliary lines rt displaying device for displaying a section fc of the second volumetric data v selected by the operator, a curve r which results from the crossing of said section fc and a spherical surface R having (the distance between the reference points AC)×(the distance between the connection points ab)÷(the distance between the reference points AB) as its radius and the connection point a as its center, and a curve t which results from the crossing of said section fc and a spherical surface T having (the distance between the reference points BC)×(the distance between the connection points ab)÷(the distance between the reference points AB) as its radius and the connection point b as its center;
a connection point c determining device for having the operator determine a connection point c corresponding to said reference point C on said section fc; and
a coordinate adjusting device for adjusting the coordinates of said first volumetric data V and said second volumetric data v such that said reference points A, B and C and said connection points a, b and c have respectively the same coordinates.

2. The volumetric data connecting apparatus according to claim 1, further comprising an intersection displaying device for displaying the section fc of the second volumetric data v selected by the operator and the intersection between the curve r and the curve t.

3. The volumetric data connecting apparatus according to claim 1, wherein said second volumetric data v comprises a plurality of frames and said section fc is one of the frames.

4. The volumetric data connecting apparatus according to claim 1, further comprising a volumetric data capturing device for capturing from outside said first volumetric data V and said second volumetric data v.

5. The volumetric data connecting apparatus according to claim 1, further comprising a volumetric data capturing device for capturing from an image diagnostic apparatus said first volumetric data V and said second volumetric data v.

6. A volumetric data connecting method comprising:
a reference point determining step for having an operator determine reference points A, B and C which are not on the same straight line on first volumetric data V;
a connection points ab determining step for having the operator determine a connection point a corresponding to said reference point A and a connection point b corresponding to said reference point B on second volumetric data v;
an auxiliary lines rt displaying step for displaying a section fc of the second volumetric data v selected by the operator, a curve r which results from the crossing of said section fc and a spherical surface R having (the distance between the reference points AC)×(the distance between the connection points ab)÷(the distance between the reference points AB) as its radius and the connection point a as its center, and a curve t which results from the crossing of said section fc and a spherical surface T having (the distance between the reference points BC)×(the distance between the connection points ab)÷(the distance between the reference points AB) as its radius and the connection point b as its center;
a connection point c determining step for having the operator determine a connection point c corresponding to said reference point C on said section fc; and
a coordinate adjusting step for adjusting the coordinates of said first volumetric data V and said second volumetric data v such that said reference points A, B and C and said connection points a, b and c have respectively the same coordinates.

7. The volumetric data connecting method according to claim 6, further comprising an intersection displaying step for displaying the section fc of the second volumetric data v selected by the operator and the intersection between the curve r and the curve t.

8. The volumetric data connecting method according to claim 6, wherein said second volumetric data v comprises a plurality of frames and said section fc is one of the frames.

9. The volumetric data connecting method according to claim 6, further comprising a volumetric data capturing step for capturing from outside said first volumetric data V and said second volumetric data v.

10. The volumetric data connecting method according to claim 6, further comprising a volumetric data capturing step for capturing by an image diagnostic method said first volumetric data V and said second volumetric data v.

11. A volumetric data connecting apparatus comprising:
a reference point determining device for having an operator determine reference points A, B and C which are not on the same straight line on first volumetric data V;
a connection point a determining device for having the operator determine a connection point a corresponding to said reference point A on second volumetric data v;
an auxiliary line q displaying device for displaying a section fb of the second volumetric data v selected by the operator and a curve q which results from the crossing of said section fb and a spherical surface Q having the distance between the reference points AB as its radius and the connection point a as its center;
a connection point b determining device for having the operator determine a connection point b corresponding to said reference point B on said section fb;
an auxiliary lines rt displaying device for displaying a section fc of the second volumetric data v selected by the operator, a curve r which results from the crossing of said section fc and a spherical surface R having the distance between the reference points AC as its radius and the connection point a as its center and a curve t which results from the crossing of said section fc and a spherical surface T having the distance between the reference points BC as its radius and the connection point b as its center;
a connection point c determining device for having the operator determine a connection point c corresponding to said reference point C on said section fc; and
a coordinate adjusting device for adjusting the coordinates of said first volumetric data V and said second volumetric data v such that said reference points A, B and C and said connection points a, b and c have respectively the same coordinates.

12. The volumetric data connecting apparatus according to claim 11, further comprising an intersection displaying device for displaying the section fc of the second volumetric data v selected by the operator and the intersection between the curve r and the curve t.

13. The volumetric data connecting apparatus according to claim 11, wherein said second volumetric data v comprises a plurality of frames and each of said sections fb and fc is one of the frames.

14. The volumetric data connecting apparatus according to claim 11, further comprising a volumetric data capturing device for capturing from outside said first volumetric data V and said second volumetric data v.

15. The volumetric data connecting apparatus according to claim 11, further comprising a volumetric data capturing device for capturing from an image diagnostic apparatus said first volumetric data V and said second volumetric data v.

16. A volumetric data connecting method comprising:
a reference point determining step for having an operator determine reference points A, B and C which are not on the same straight line on first volumetric data V;
a connection point a determining step for having the operator determine a connection point a corresponding to said reference point A on second volumetric data v;
an auxiliary line q displaying step for displaying a section fb of the second volumetric data v selected by the operator and a curve q which results from the crossing of said section fb and a spherical surface Q having the distance between the reference points AB as its radius and the connection point a as its center;
a connection point b determining step for having the operator determine a connection point b corresponding to said reference point B on said section fb;
an auxiliary lines rt displaying step for displaying a section fc of the second volumetric data v selected by the operator, a curve r which results from the crossing of said section fc and a spherical surface R having the distance between the reference points AC as its radius and the connection point a as its center and a curve t which results from the crossing of said section fc and a spherical surface T having the distance between the reference points BC as its radius and the connection point b as its center;
a connection point c determining step for having the operator determine a connection point c corresponding to said reference point C on said section fc; and a coordinate adjusting step for adjusting the coordinates of said first volumetric data V and said second volumetric data v such that said reference points A, B and C and said connection points a, b and c have respectively the same coordinates.

17. The volumetric data connecting method according to claim 16, further comprising an intersection displaying step for displaying the section fc of the second volumetric data v selected by the operator and the intersection between the curve r and the curve t.

18. The volumetric data connecting method according to claim 16, wherein said second volumetric data v comprises a plurality of frames and each of said sections fb and fc is one of the frames.

19. The volumetric data connecting method according to claim 16, further comprising a volumetric data capturing step for capturing from outside said first volumetric data V and said second volumetric data v.

20. The volumetric data connecting method according to claim 16, further comprising a volumetric data capturing step for capturing by an image diagnostic method said first volumetric data V and said second volumetric data v.

* * * * *